US006127332A

United States Patent [19]
Goelz et al.

[11] Patent Number: 6,127,332
[45] Date of Patent: Oct. 3, 2000

[54] MUTEINS OF IFN-β

[75] Inventors: Susan E. Goelz, Winchester; Richard L. Cate, Cambridge; E. Pingchang Chow, Charlestown; R. Blake Pepinsky, Watertown, all of Mass.

[73] Assignee: Biogen, Inc., Cambridge, Mass.

[21] Appl. No.: 08/912,768

[22] Filed: Aug. 18, 1997

Related U.S. Application Data

[63] Continuation of application No. 08/475,774, Jun. 7, 1995, abandoned, which is a continuation of application No. 08/213,448, Mar. 15, 1994, Pat. No. 5,545,723.

[51] Int. Cl.$^7$ .............................. A61K 38/00; C12N 15/24
[52] U.S. Cl. ........................... 514/2; 435/375; 435/320.1; 530/350
[58] Field of Search ....................... 514/44, 2; 435/320.1, 435/375, 69.1; 424/93.21; 530/350

[56] References Cited

PUBLICATIONS

Aulitzky, W.E. et al., Recombinant interferon beta in chronic myelogenous leukemia, Sem. Hemat. 30, pp. 14–16 (1993).

Basso, P. and Verdi, F., Trattamento con beta–interferone nelle infezioni da HPV dell'apparato genitale femminile, Minerva Ginecol. 44, pp. 181–184 (1992) (Abstract in English).

Cimino, T. et al., Forme istologiche di epatite cronica e risposta al trattamento con interferoni, Minerva Med 84, pp. 681–685 (1993) (Abstract in English).

Duggan, D.B. et al., A phase II study of recombinant interleukin–2 with or without recombinant interferon–β in non–Hodgkins lymphoma. A study of the cancer and Leukemia group B, Journal of Immunotherapy 12, pp. 115–122 (1992).

Gomi, K. et al., Antitumor effect of human recombinant interferon–λ and β against human osteosarcoma transplanted into nude mice, J. Pharmacobio–Dyn. 9, pp. 879–888 (1986).

Gresser, I., Pronounced Antiviral Activity of Human Interferon on Bovine and Porcine Cells, Nature, 251, pp. 543–545 (1974).

Hertzog, Paul J., et al., Role of Interferons in the Regulation of Cell Proliferation, Differentiation, and Development, Molecular Reproduction and Development, 39, pp. 226–232 (1994).

Higgins, P.G. et al., Interferon–$β_{ser}$ as phrophylaxis against experimental rhinovirus infection in volunteers, Journal of Interferon Research 6, pp. 153–159 (1986).

Horoszewicz, J.S. et al., Human Fibroblast Interferon in Human Neoplasia: Clinical and Laboratory Study, Cancer Treatment Reports, 62, pp. 1899–1906 (1978).

Jacobs, L.D. Intramuscular Interferon Beta–1a For Disease Progression in Relapsing Multiple Sclerosis, Annals of Neurology, 39(3), pp. 285–294 (1996).

Kinney, P. et al., Phase II trial of Interferon–beta–serine in metastatic renal cell carcinoma, J. Clin. Oncol. 8, pp. 881–885 (1990).

Kunder, S.C. et al., Biological response modifier–mediated resistance to herpesvirus infections requires induction of α/β interferon, Antiviral Research 21, pp. 129–139 (1993).

Nemato, T. et al., Human Interferons and Intralesional Therapy of Melanoma and Breast Carcinoma (Proceedings of AACR and ASCO), Abstract 993, p. 246.

Ohno, R., Interferons in the treatment of multiple myeloma, Int. J. Cancer Suppl. 1, pp. 14–20 (1987).

Ozzello, L. et al., Antiproliferative effects of natural interferon beta alone and in combination with natural interferon gamma on breast carcinomas in nude mice, Breast Cancer Research 16, pp. 89–96 (1990).

Paty, D.W. et al., Interferon beta–1b is effective in relapsing–remitting multiple sclerosis, Neurology 43, pp. 662–667 (1993).

Schmidt, C.A. et al., Detection of allelic loss within β1–interferon gene in childhood acute lymphoblastic leukemial using differential PCR, Ann. Hemat. 68, pp. 171–174 (1994).

Shephard, H. Michael, et al., A Single Amino Acid Change in IFN–$β_1$ Abolishes its Antiviral Activity, Nature, 294, pp. 563–565 (Dec. 1981).

Sica, G. et al., Effect of natural beta–interferon on cell proliferation and steroid receptor level in human breast cancer cells, Cancer 60, pp. 2419–2423 (1987).

Stuzziero, E. and Corbo, M., Il beta interferone nella pratica clinica, Minerva Ginecol. 46, pp. 487–489 (1994) (Abstract in English).

Stuart–Harris, R.C. et al., The clinical application of the interferons: a review, The Medical Journal of Australia 156, pp. 869–872 (1992).

Torigoe, S. et al., Cytofluorographic analysis of effects of interferons on expression of human cytomegalovirus proteins, Journal of Virological Methods 45, pp. 219–228 (1993).

Wiernik, P.H. et al., Successful treatment of Hairy Cell Leukemia with β–ser interferon, American Journal of Hematology 33, pp. 244–248 (1990).

Winkler, K. et al., Treatment of osteosarcoma: Experience of the cooperative osteosarcoma study group (COSS), Osteosarcoma in adolescents and young adults, Cancer treatment and Research 62, pp. 269–277 (1993).

(List continued on next page.)

Primary Examiner—Karen M. Hauda
Attorney, Agent, or Firm—Fish & Neave; James F. Hanley, Jr.; Scott D. Miller

[57] ABSTRACT

A IFN-β mutein in which phe (F), tyr (Y), trp (W) or his (H) is substituted for val (V) at position 101, when numbered in accordance with wild type IFN-β, DNA sequences encoding these IFN-β muteins, recombinant DNA molecules containing those DNA sequences operatively linked to expression control sequences and capable of inducing expression of an IFN-β mutein, hosts transformed with those recombinant DNA molecules, pharmaceutical compositions containing IFN-β muteins and methods for treating viral infections, cancer or tumors, undesired cell proliferation, or for immunomodulation.

8 Claims, 5 Drawing Sheets

OTHER PUBLICATIONS

Wintergerst, U. and Belohradsky, B.H., Acyclovir monotherapy versus Acyclovir plus Beta–Interferon in focal viral encaphalitis in children, *Infection* 20, pp. 207–212 (1992).

Worm, M. et al., Responsiveness to interferon treatment of human melanoma cells correlates to immunophenotype, *Melanoma Research* 3, pp. 29–33 (1993).

Wu, S. et al., A study on the relationship between the N terminal variation of human interferon β and its antiviral activity, *Immunochemistry* 109, p. 515 (1988) (abstract only).

Yung, W.K.A., et al., A pilot study of recombinant interferon beta (IFN-$\beta_{ser}$) in patients with recurrent glioma, *Journal of Neuro–Oncology* 9, pp. 29–34 (1990).

The Houston Chronicle, May 28, 1996. "Patients Suffering from MS Now Have Second Drug Option".

The New York Times, May 18, 1996. "F.D.A. Approves a Biogen Drug for Treating Multiple Sclerosis".

Wall Street Journal, May 20, 1996. "New Drug Aims to Win Over MS Sufferers".

USA Today, May 20, 1996. "Second MS Drug Now On the Market".

MSYNLLGFLT QRSSNFQCQKL
LWQLNGRLEY CLKDRMNFDI
PEEIKQLQQA FQKEDAALTIY
EMLQNIFAIF RQDSSTGWN
ETIVENLLAN VYHQINHLKT
FLEEKLEKED FTRGKLMSL
HLKRYYGRI LHYLKAKEYSH
CAWTIVRVEI LRNFYFINRL
TGYLRN

FIG. 1

```
            -20                -15                -10                 -5
ATGACCAACAAGTGTCTCCTCCAAATTGCTCTCCTGTTGTGCTTCTCCACTACAGCT
 M   T   N   K   C   L   L   Q   I   A   L   L   L   C   F   S   T   T   A 1                  5                 10                 15
CTTTCCATGAGCTACAACTTGCTTGGATTCCTACAAAGAAGCAGCAATTTTCAGTGT
 L   S   M   S   Y   N   L   L   G   F   L   Q   R   S   S   N   F   Q   C 20                 25                 30                 35
CAGAAGCTCCTGTGGCAATTGAATGGGAGGCTTGAATACTGCCTCAAGGACAGGATG
 Q   K   L   L   W   Q   L   N   G   R   L   E   Y   C   L   K   D   R   M 40                 45                 50                 55
AACTTTGACATCCCTGAGGAGATTAAGCAGCTGCAGCAGTTCCAGAAGGAGGACGCC
 N   F   D   I   P   E   E   I   K   Q   L   Q   Q   F   Q   K   E   D   A 60                 65                 70
GCATTGACCATCTATGAGATGCTCCAGAACATCTTTGCTATTTTCAGACAAGATTCA
 A   L   T   I   Y   E   M   L   Q   N   I   F   A   I   F   R   Q   D   S 75                 80                 85                 90
TCTAGCACTGGCTGGAATGAGACTATTGTTGAGAACCTCCTGGCTAATGTCTATCAT
 S   S   T   G   W   N   E   T   I   V   E   N   L   L   A   N   V   Y   H 95                100                105                110
CAGATAAACCATCTGAAGACATTCCTGGAAGAAAAACTGGAGAAAGAAGATTTCACC
 Q   I   N   H   L   K   T   F   L   E   E   K   L   E   K   E   D   F   T 115                120                125                130
AGGGGAAAACTCATGAGCAGTCTGCACCTGAAAAGATATTATGGGAGGATTCTGCAT
 R   G   K   L   M   S   S   L   H   L   K   R   Y   Y   G   R   I   L   H 135                140                145                150
TACCTGAAGGCCAAGGAGTACAGTCACTGTGCCTGGACCATAGTCAGAGTGGAAATC
 Y   L   K   A   K   E   Y   S   H   C   A   W   T   I   V   R   V   E   I 155                160                165
CTAAGGAACTTTTACTTCATTAACAGACTTACAGGTTACCTCCGAAAC
 L   R   N   F   Y   F   I   N   R   L   T   G   Y   L   R   N
```

FIG. 2

MUTEINS OF IFN-β

This is a continuation of application Ser. No. 08/475,774, filed Jun. 7, 1995, entitled NOVEL MUTEINS OF IFN-β, now abandoned; which is a continuation of U.S. patent application Ser. No. 08/213,448, filed Mar. 15, 1994, now U.S. Pat. No. 5,545,723 issued Aug. 13, 1996.

TECHNICAL FIELD OF THE INVENTION

This invention relates to muteins of interferon-beta ("IFN-β") in which val (V) at position 101, when numbered in accordance with wild type IFN-β, is substituted with phe (F), trp (W), tyr (Y) or his (H).

BACKGROUND OF THE INVENTION

Interferons are single chain polypeptides secreted by most animal cells in response to a variety of inducers, including viruses, mitogens and polynucleotides. Interferons participate in regulation of cell function, and have antiviral, antiproliferative and immunomodulating properties. Native human interferons are classified into three major types: α-IFN (leukocyte), IFN-β (fibroblast) and γ-IFN (immune). Native IFN-β is produced primarily by diploid fibroblast cells and in lesser amounts by lymphoblastoid cells.

IFN-β is a glycoprotein. Its nucleic acid and amino acid sequences have been determined. (Houghton et al., "The Complete Amino Acid Sequence of Human Fibroblast Interferon as Deduced Using Synthetic Oligodeoxyribonucleotide Primers of Reverse Transcriptase," *Nucleic Acids Research*, 8, pp. 2885–94 (1980); T. Taniguchi et al., "The Nucleotide Sequence of Human Fibroblast DNA," *Gene*, 10, pp. 11–15 (1980)). Recombinant IFN-β has been produced and characterized.

IFN-β exhibits various biological and immunological activities. One of IFN-β's biological activities is its antiviral activity. This antiviral activity can be neutralized by antibodies to IFN-β. See EP-B1-41313. Preparation and purification of antibodies to IFN-β is described in EP-B1-41313 and the references cited therein. IFN-β is also able to bind to cells that express interferon receptors, such as Daudi cells or A549 cells.

As a result of these activities, IFN-β has potential applications in immunotherapy, antitumor and anticancer therapies, and antiviral therapies.

Numerous investigations and clinical trials have been and continue to be conducted into the antitumor and anticancer properties of both wild type and recombinant IFN-β. These include treatment of several malignant diseases such as osteosarcoma, basal cell carcinoma, cervical dysplasia, glioma, acute myeloid leukemia, multiple myeloma and Hodgkin's disease. In addition, IFN-β has been shown to cause local tumor regression when injected into subcutaneous tumoral nodules in melanoma and breast carcinoma-affected patients.

IFN-β (wild-type and recombinant) has been tested clinically in a variety of viral infections, including papilloma viruses, such as genital warts and condylomata of the uterine cervix; viral hepatitis, including acute/chronic hepatitis B and non-A, non-B hepatitis (hepatitis C); herpes genitalis; herpes zoster; herpetic keratitis; herpes simplex; viral encephalitis; cytomegalovirus pheumonia; and in the prophylaxis of rhinovirus.

Clinical trials using recombinant IFN-β in the treatment of multiple sclerosis have also been conducted and IFN-β is approved for sale in the United States for the treatment of multiple sclerosis.

SUMMARY OF THE INVENTION

This invention provides muteins of IFN-β wherein the val (V) at position 101, when numbered in accordance with wild type IFN-β, is substituted with phe (F), tyr (Y), trp (W), or his (H). This invention also provides DNA sequences encoding these IFN-β muteins, recombinant DNA molecules containing those sequences operatively linked to expression control sequences and capable of inducing, in an appropriate host, the expression of the IFN-β muteins, hosts transformed with those recombinant DNA molecules and pharmaceutical compositions containing the IFN-β. These compositions are useful in immunotherapy as well as in anticancer, antitumor and antiviral therapies.

BRIEF DESCRIPTION OF THE DRAWINGS

FIG. 1 depicts the amino acid sequence of the preferred mutein of this invention IFN-β(phe$_{101}$) (SEQ ID NO: 1).

FIG. 2 depicts the preferred degenerate DNA sequence encoding IFN-β(phe$_{101}$) and the signal sequence of native IFN-β (SEQ ID NO: 2).

DETAILED DESCRIPTION OF THE INVENTION

Figure 3A:
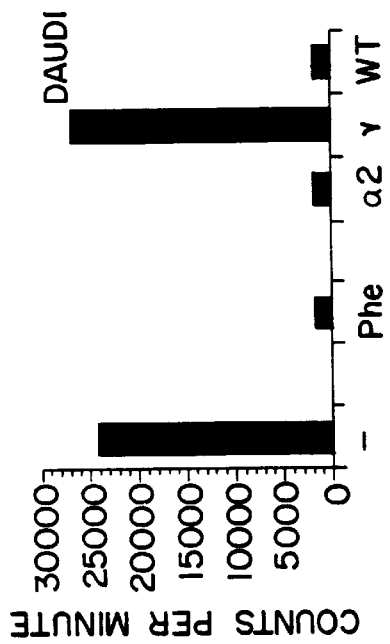
FIG. 3 shows an analysis of IFN-β(phe$_{101}$) binding to interferon receptor bearing cells. Panels A and B show receptor binding data for $^{125}$I-IFN-β(phe$_{101}$) and wild type $^{125}$I-IFN-β, respectively, to Daudi cells. Panels C and D show receptor binding data for $^{125}$I-IFN-β(phe$_{101}$) and wild type $^{125}$I-IFN-β, respectively, to A549 cells.
Figure 3B:
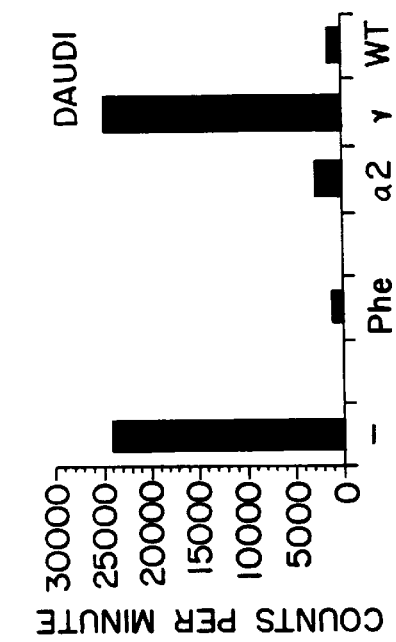
Figure 3C:
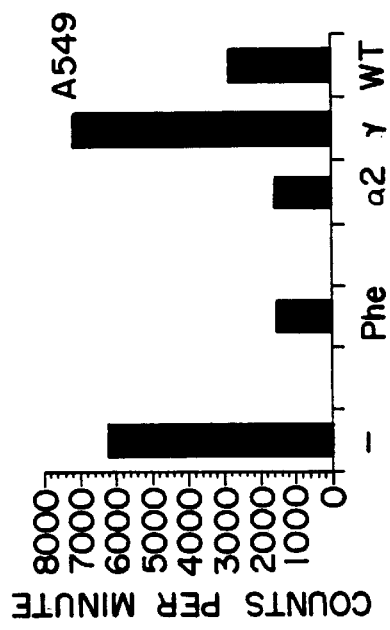
Figure 3D:
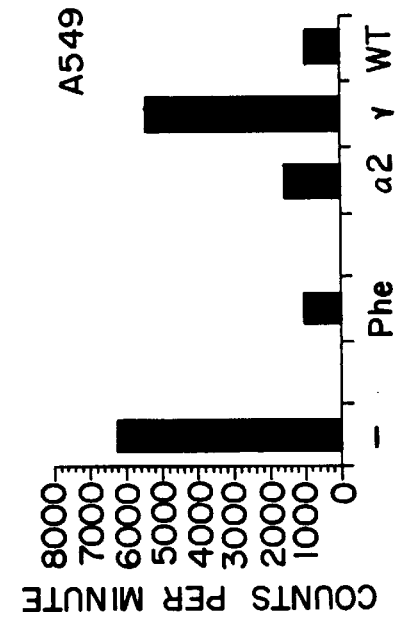
Figure 4A:
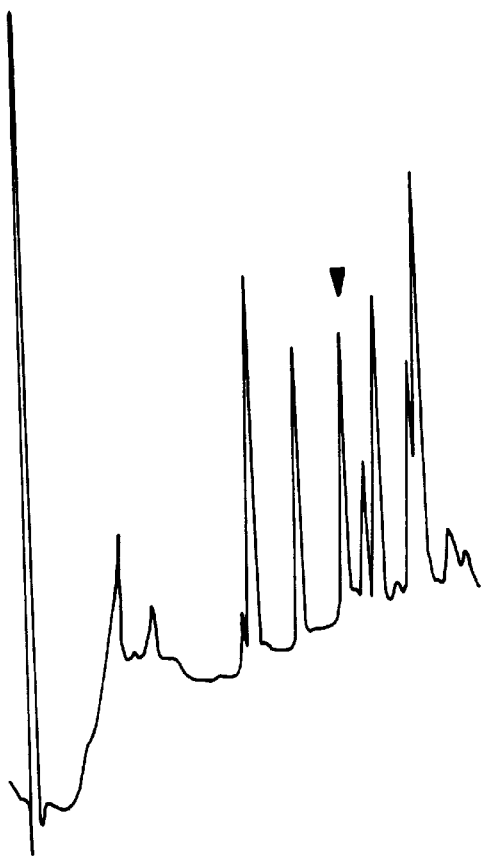
FIG. 4 shows an analysis of IFN-β(phe$_{101}$) and wild type IFN-β by peptide mapping by endoproteinase Lyse-C.
Figure 4B:
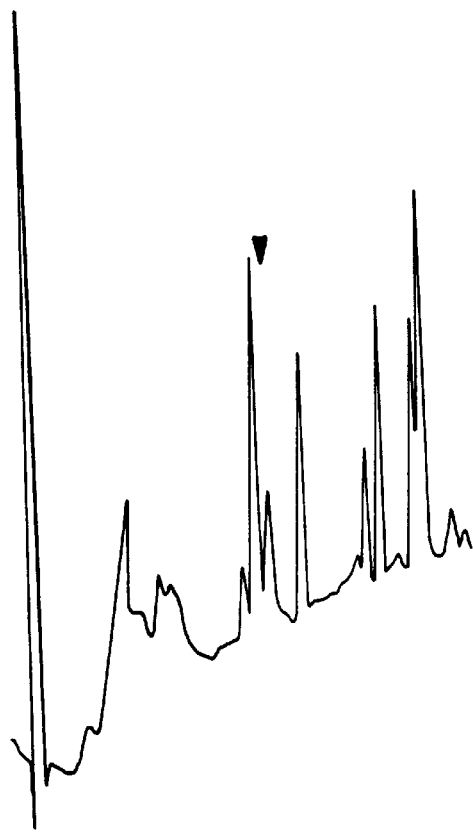

As used herein, "wild type IFN-β" means an IFN-β, whether native or recombinant, having the normally occurring amino acid sequence of native human IFN-β, as shown, e.g., in EP-B1-41313, FIG. 4.

As used herein, "IFN-β mutein" means a polypeptide wherein the val (V) at position 101, when numbered in accordance with wild type IFN-β, is substituted with phe (F), tyr (Y), trp (W), or his (H), preferably phe (F). Our most preferred IFN-β muteins have an amino acid sequence identical to wild type IFN-β at the other residues. However, the IFN-β muteins of this invention may also be characterized by amino acid insertions, deletions, substitutions and modifications at one or more sites in or at the other residues of the native IFN-β polypeptide chain. In accordance with this invention any such insertions, deletions, substitutions and modifications result in an IFN-β mutein that retains an antiviral activity that can be at least partially neutralized by antibodies to wild type IFN-β.

We prefer conservative modifications and substitutions (i.e., those that have a minimal effect on the secondary or tertiary structure of the mutein). Such conservative substitutions include those described by Dayhoff in the *Atlas of Protein Sequence and Structure* 5 (1978), and by Argos in *EMBO J.*, 8, 779–785 (1989). For example, amino acids belonging to one of the following groups represent conservative changes:

ala, pro, gly, gln, asn, ser, thr;

cys, ser, tyr, thr;

val, ile, leu, met, ala, phe;

lys, arg, his; and phe, tyr, trp, his.

We also prefer modifications or substitutions that eliminate sites for intermolecular crosslinking or incorrect disulfide bond formation. For example, IFN-β is known to have three cys residues, at wild-type positions 17, 31 and 141. U.S. Pat. No. 4,588,585 refers to an IFN-β mutein in which the cys (C) at position 17 has been substituted with ser (S). This substitution can also be utilized in this invention. For example, this invention contemplates an IFN-β mutein having ser (S) substituted for cys (C) at position 17 and val (V) at position 101 substituted with phe (F), trp (W), tyr (Y), or his (H), preferably phe (F), when numbered in accordance with wild type IFN-β.

By "numbered in accordance with wild type IFN-β" we mean identifying a chosen amino acid with reference to the position at which that amino acid normally occurs in wild type IFN-β. Where insertions or deletions are made to the IFN-β mutein, one of skill in the art will appreciate that the val (V) normally occuring at position 101, when numbered in accordance with wild type IFN-β, may be shifted in position in the mutein. However, the location of the shifted val (V) can be readily determined by inspection and correlation of the flanking amino acids with those flanking $val_{101}$ in wild type IFN-β.

The IFN-β muteins of the present invention can be produced by any suitable method known in the art. Such methods include constructing a DNA sequence encoding the IFN-β muteins of this invention and expressing those sequences in a suitable transformed host. This method will produce recombinant muteins of this invention. However, the muteins of this invention may also be produced, albeit less preferably, by chemical synthesis or a combination of chemical synthesis and recombinant DNA technology.

In one embodiment of a recombinant method for producing a mutein of this invention, a DNA sequence is constructed by isolating or synthesizing a DNA sequence encoding the wild type IFN-β and then changing the codon for $val_{101}$ to a codon for phe (F), trp (W), tyr (Y) or his (H), preferably phe (F), by site-specific mutagenesis. This technique is well known. See, e.g., Mark et al., "Site-specific Mutagenesis Of The Human Fibroblast Interferon Gene", *Proc. Natl. Acad. Sci. USA,* 81, pp. 5662–66 (1984); U.S. Pat. No. 4,588,585, incorporated herein by reference.

Another method of constructing a DNA sequence encoding the IFN-β muteins of this invention would be chemical synthesis. For example, a gene which encodes the desired IFN-β mutein may be synthesized by chemical means using an oligonucleotide synthesizer. Such oligonucleotides are designed based on the amino acid sequence of the desired IFN-β mutein, and preferably selecting those codons that are favored in the host cell in which the recombinant mutein will be produced. In this regard, it is well recognized that the genetic code is degenerate—that an amino acid may be coded for by more than one codon. For example, phe (F) is coded for by two codons, TTC or TTT, tyr (Y) is coded for by TAC or TAT and his (H) is coded for by CAC or CAT. Trp (W) is coded for by a single codon, TGG. Accordingly, it will be appreciated that for a given DNA sequence encoding a particular IFN-β mutein, there will be many DNA degenerate sequences that will code for that IFN-β mutein. For example, it will be appreciated that in addition to the preferred DNA sequence shown in FIG. 2, there will be many degenerate DNA sequences that code for the IFN-β mutein shown in FIG. 1. These degenerate DNA sequences are considered within the scope of this invention.

The DNA sequence encoding the IFN-β mutein of this invention, whether prepared by site directed mutagenesis, synthesis or other methods, may or may not also include DNA sequences that encode a signal sequence. Such signal sequence, if present, should be one recognized by the cell chosen for expression of the IFN-β mutein. It may be prokaryotic, eukaryotic or a combination of the two. It may also be the signal sequence of native IFN-β. The inclusion of a signal sequence depends on whether it is desired to secrete the IFN-β mutein from the recombinant cells in which it is made. If the chosen cells are prokaryotic, it generally is preferred that the DNA sequence not encode a signal sequence. If the chosen cells are eukaryotic, it generally is preferred that a signal sequence be encoded and most preferably that the wild-type IFN-β signal sequence be used.

Standard methods may be applied to synthesize a gene encoding an IFN-β mutein according to this invention. For example, the complete amino acid sequence may be used to construct a back-translated gene. A DNA oligomer containing a nucleotide sequence coding for IFN-β mutein may be synthesized. For example, several small oligonucleotides coding for portions of the desired polypeptide may be synthesized and then ligated. The individual oligonucleotides typically contain 5' or 3' overhangs for complementary assembly.

Once assembled (by synthesis, site directed mutagenesis or another method), the DNA sequences encoding an IFN-β mutein of this invention will be inserted into an expression vector and operatively linked to an expression control sequence appropriate for expression of the IFN-β mutein in the desired transformed host. Proper assembly may be confirmed by nucleotide sequencing, restriction mapping, and expression of a biologically active polypeptide in a suitable host. As is well known in the art, in order to obtain high expression levels of a transfected gene in a host, the gene must be operatively linked to transcriptional and translational expression control sequences that are functional in the chosen expression host.

The choice of expression control sequence and expression vector will depend upon the choice of host. A wide variety of expression host/vector combinations may be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from *E. coli,* including col E1, pCR1, pBR322, pMB9 and their derivatives, wider host range plasmids, such as RP4, phage DNAs, e.g., the numerous derivatives of phage lambda, e.g., NM989, and other DNA phages, such as M13 and filamentous single stranded DNA phages. Useful expression vectors for yeast cells include the 2μ plasmid and derivatives thereof. Useful vectors for insect cells include pVL 941. We prefer pBG311. Cate et al., "Isolation Of The Bovine And Human Genes For Mullerian Inhibiting Substance And Expression Of The Human Gene In Animal Cells", *Cell,* 45, pp. 685–98 (1986).

In addition, any of a wide variety of expression control sequences may be used in these vectors. Such useful expression control sequences include the expression control sequences associated with structural genes of the foregoing expression vectors. Examples of useful expression control sequences include, for example, the early and late promoters of SV40 or adenovirus, the lac system, the trp system, the TAC or TRC system, the major operator and promoter regions of phage lambda, for example PL, the control regions of fd coat protein, the promoter for 3-phosphoglycerate kinase or other glycolytic enzymes, the promoters of acid phosphatase, e.g., Pho5, the promoters of the yeast α-mating system and other sequences known to control the expression of genes of prokaryotic or eukaryotic cells or their viruses, and various combinations thereof.

Any suitable host may be used to produce the IFN-β muteins of this invention, including bacteria, fungi (including yeasts), plant, insect, mammal, or other appropriate animal cells or cell lines, as well as transgenic animals or plants. More particularly, these hosts may include well known eukaryotic and prokaryotic hosts, such as strains of *E. coli,* Pseudomonas, Bacillus, Streptomyces, fungi, yeast, insect cells such as *Spodoptera fruaiperda* (SF9), animal cells such as Chinese hamster ovary (CHO) and mouse cells such as NS/0, African green monkey cells such as COS 1, COS 7, BSC 1, BSC 40, and BMT 10, and human cells, as well as plant cells in tissue culture. For animal cell expression, we prefer CHO cells and COS 7 cells in cultures and particularly the CHO-DDUKY-β1 cell line (infra, pp. 18–19).

It should of course be understood that not all vectors and expression control sequences will function equally well to express the DNA sequences described herein. Neither will all hosts function equally well with the same expression system. However, one of skill in the art may make a selection among these vectors, expression control sequences and hosts without undue experimentation. For example, in selecting a vector, the host must be considered because the vector must replicate in it. The vector's copy number, the ability to control that copy number, and the expression of any other proteins encoded by the vector, such as antibiotic markers, should also be considered. For example, preferred vectors for use in this invention include those that allow the DNA encoding the IFN-β muteins to be amplified in copy number. Such amplifiable vectors are well known in the art. They include, for example, vectors able to be amplified by DHFR amplification (see, e.g., Kaufman, U.S. Pat. No. 4,470,461, Kaufman and Sharp, "Construction Of A Modular Dihydrafolate Reductase cDNA Gene: Analysis Of Signals Utilized For Efficient Expression", *Mol. Cell. Biol.,* 2, pp. 1304–19 (1982)) or glutamine synthetase ("GS") amplification (see, e.g., U.S. Pat. No. 5,122,464 and European published application 338,841).

In selecting an expression control sequence, a variety of factors should also be considered. These include, for example, the relative strength of the sequence, its controllability, and its compatibility with the actual DNA sequence encoding the IFN-β mutein of this invention, particularly as regards potential secondary structures. Hosts should be selected by consideration of their compatibility with the chosen vector, the toxicity of the product coded for by the DNA sequences of this invention, their secretion characteristics, their ability to fold the polypeptides correctly, their fermentation or culture requirements, and the ease of purification of the products coded for by the DNA sequences.

Within these parameters, one of skill in the art may select various vector/expression control sequence/host combinations that will express the desired DNA sequences on fermentation or in large scale animal culture, for example, using CHO cells or COS 7 cells.

The IFN-β muteins obtained according to the present invention may be glycosylated or unglycosylated depending on the host organism used to produce the mutein. If bacteria are chosen as the host then the IFN-β mutein produced will be unglycosylated. Eukaryotic cells, on the other hand, will glycosylate the IFN-β muteins, although perhaps not in the same way as native IFN-β is glycosylated.

The IFN-β mutein produced by the transformed host can be purified according to any suitable method. Various methods are known for purifying IFN-β. See, e.g., U.S. Pat. Nos. 4,289,689, 4,359,389, 4,172,071, 4,551,271, 5,244,655, 4,485,017, 4,257,938 and 4,541,952. We prefer immunoaffinity purification. See, e.g., Okamura et al., "Human Fibroblastoid Interferon: Immunosorbent Column Chromatography And N-Terminal Amino Acid Sequence", *Biochem.,* 19, pp. 3831–35 (1980).

The biological activity of the IFN-β muteins of this invention can be assayed by any suitable method known in the art. Such assays include antibody neutralization of antiviral activity, induction of protein kinase, oligoadenylate 2,5-A synthetase or phosphodiesterase activities, as described in EP-B1-41313. Such assays also include immunomodulatory assays (see, e.g., U.S. Pat. No. 4,753,795), growth inhibition assays, and measurement of binding to cells that express interferon receptors.

The IFN-β mutein of this invention will be administered at a dose approximately paralleling that employed in therapy with wild type native or recombinant IFN-β. An effective amount of the IFN-β mutein is preferably administered. An "effective amount" means an amount capable of preventing or lessening the severity or spread of the condition or indication being treated. It will be apparent to those of skill in the art that the effective amount of IFN-β mutein will depend, inter alia, upon the disease, the dose, the administration schedule of the IFN-β mutein, whether the IFN-β mutein is administered alone or in conjunction with other therapeutic agents, the serum half-life of the composition, and the general health of the patient.

The IFN-β mutein is preferably administered in a composition including a pharmaceutically acceptable carrier. "Pharmaceutically acceptable carrier" means a carrier that does not cause any untoward effect in patients to whom it is administered. Such pharmaceutically acceptable carriers are well known in the art. We prefer human serum albumin.

The IFN-β muteins of the present invention can be formulated into pharmaceutical compositions by well known methods. See, e.g., Remington's Pharmaceutical Sciences by E. W. Martin, hereby incorporated by reference, describes suitable formulations. The pharmaceutical composition of the IFN-β mutein may be formulated in a variety of forms, including liquid, gel, lyophilized, or any other suitable form. The preferred form will depend upon the particular indication being treated and will be apparent to one of skill in the art.

The IFN-β mutein pharmaceutical composition may be administered orally, intravenously, intramuscularly, intraperitoneally, intradermally or subcutaneously or in any other acceptable manner. The preferred mode of administration will depend upon the particular indication being treated and will be apparent to one of skill in the art.

The pharmaceutical composition of the IFN-β mutein may be administered in conjunction with other therapeutic agents. These agents may be incorporated as part of the same pharmaceutical composition or may be administered separately from the IFN-β mutein, either concurrently or in accordance with any other acceptable treatment schedule. In addition, the IFN-β mutein pharmaceutical composition may be used as an adjunct to other therapies.

Accordingly, this invention provides compositions and methods for treating viral infections, cancers or tumors, abnormal cell growth, or for immunomodulation in any suitable animal, preferably a mammal, most preferably human.

Also contemplated is use of the DNA sequences encoding the IFN-β muteins of this invention in gene therapy applications.

Gene therapy applications contemplated include treatment of those diseases in which IFN-β is expected to provide an effective therapy due to its antiviral activity, e.g., viral diseases, including hepatitis, and particularly HBV or HCV, or other infectious diseases that are responsive to IFN-β or infectious agents sensitive to IFN-β. Five distinct hepatitis viruses have been isolated and cloned; hepatitis A, B, C, D, and E. One of the target tissues for treatment of viral hepatitis using gene therapy is hepatocytes in the liver.

Similarly, this invention contemplates gene therapy applications for immunomodulation, including treatment of lupus and multiple sclerosis.

This invention also contemplates gene therapy applications for the treatment of those diseases in which IFN-β is expected to provide an effective therapy due to its antiproliferative activity, e.g., tumors and cancers, or other conditions characterized by undesired cell proliferation, such as restenosis. Among the cancers contemplated for gene therapy treatment are gliomas, meningioma, malignant carcinoid, basal cell carcinoma, melanoma, squamous cell carcinoma, hemangioma, leukemia (including hairy cell leukemia and chronic myeloid leukemia), lymphomas (including cutaneous T Cell lymphoma and Hodgkin's lymphoma), myelomas (including multiple myeloma), renal cell carcinoma, osteosarcoma, colorectal cancer, prostate cancer, ovarian cancer, cervical carcinoma, non-small cell lung carcinoma, and breast cancer. We specifically contemplate treatment of glioma and melanoma.

Local delivery of IFN-β using gene therapy may provide relatively high concentrations of the therapeutic agent to the target area while avoiding potential toxicity problems associated with non-specific administration.

Both in vitro and in vivo gene therapy methodologies are contemplated.

Several methods for transferring potentially therapeutic genes to defined cell populations are known. See, e.g., Mulligan, "The Basic Science Of Gene Therapy", *Science*, 260, pp. 926–31 (1993). These methods include:

1) Direct gene transfer. See, e.g., Wolff et al., "Direct Gene transfer Into Mouse Muscle In Vivo", *Science*, 247, pp. 1465–68 (1990);

2) Liposome-mediated DNA transfer. See, e.g., Caplen at al., "Liposome-mediated CFTR Gene Transfer To The Nasal Epithelium Of Patients With Cystic Fibrosis", *Nature Med.*, 3, pp. 39–46 (1995); Crystal, "The Gene As A Drug", *Nature Med.*, 1, pp. 15–17 (1995); Gao and Huang, "A Novel Cationic Liposome Reagent For Efficient Transfection Of Mammalian Cells", *Biochem. Biophys. Res. Comm.*, 179, pp. 280–85 (1991);

3) Retrovirus-mediated DNA transfer. See, e.g., Kay et al., "In Vivo Gene Therapy Of Hemophilia B: Sustained Partial Correction In Factor IX-Deficient Dogs", *Science*, 262, pp. 117–19 (1993); Anderson, "Human Gene Therapy", *Science*, 256, pp. 808–13 (1992).

4) DNA Virus-mediated DNA transfer. Such DNA viruses include adenoviruses (preferably Ad-2 or Ad-5 based vectors), herpes viruses (preferably herpes simplex virus based vectors), and parvoviruses (preferably "defective" or non-autonomous parvovirus based vectors, more preferably adeno-associated virus based vectors, most preferably AAV-2 based vectors). See, e.g., Ali et al., "The Use Of DNA Viruses As Vectors For Gene Therapy", *Gene Therapy*, 1, pp. 367–84 (1994); U.S. Pat. No. 4,797,368, incorporated herein by reference, and U.S. Pat. No. 5,139,941, incorporated herein by reference.

The choice of a particular vector system for transferring the gene of interest will depend on a variety of factors. One important factor is the nature of the target cell population. Although retroviral vectors have been extensively studied and used in a number of gene therapy applications, these vectors are generally unsuited for infecting non-dividing cells. In addition, retroviruses have the potential for oncogenicity.

Adenoviruses have the advantage that they have a broad host range, can infect quiescent or terminally differentiated cells, such as neurons or hepatocytes, and appear essentially non-oncogenic. See, e.g., Ali et al., supra, p. 367. Adenoviruses do not appear to integrate into the host genome. Because they exist extrachromosomally, the risk of insertional mutagenesis is greatly reduced. Ali et al., supra, p. 373.

Adeno-associated viruses exhibit similar advantages as adenoviral-based vectors. However, AAVs exhibit site-specific integration on human chromosome 19. Ali et al., supra, p. 377.

In a preferred embodiment, the IFN-β mutein-encoding DNA of this invention is used in gene therapy for vascular smooth muscle cell proliferation after arterial injury. Injury of the arterial wall results in the migration of smooth muscle cells into the intimal layer of the arterial wall, where they proliferate and synthesize extracellular matrix components. See, e.g., Chang et al., "Cytostatic Gene Therapy For Vascular Proliferative Disorders With A Constitutively Active Form Of The Retinoblastoma Gene Product", *Science*, 267, p. 518 (1995). This proliferative response has been implicated in the pathogenesis of atherosclerosis.

One clinically significant setting for arterial injury follows percutaneous balloon angioplasty of the coronary arteries. Following mechanical dilation of the artery, in many cases a cellular proliferative response occurs, leading to regrowth of cells locally that impinges on the lumen and compromises blood flow. This response, known as restenosis, has not responded to conventional treatments including antiplatelet agents, angiotensin-converting enzyme antagonists, or cytotoxic drugs in humans. See, e.g., Ohno et al., "Gene Therapy For Vascular Smooth Muscle Cell Proliferation After Arterial Injury", *Science*, 265, p. 781 (1994).

According to this embodiment, gene therapy with DNA encodng the IFN-β muteins of this invention is provided to a patient in need thereof, concurrent with, or immediately after coronary balloon angioplasty. This approach takes advantage of the antiproliferative activity of the IFN-β muteins of this invention to prevent undesired SMC proliferation. The skilled artisan will appreciate that any suitable gene therapy vector containing IFN-β mutein DNA may be used in accordance with this embodiment. The techniques for constructing such a vector are known. See, e.g., Ohno et al., supra, p. 784; Chang et al., supra, p. 522. The coronary balloon angioplasty procedure is well known. Introduction of the IFN-β mutein DNA-containing vector to the target artery site may be accomplished using known techniques, e.g., as described in Ohno et al., supra, p. 784.

In order that this invention may be better understood, the following examples are set forth. These examples are for the purpose of illustration only, and are not to be construed as limiting the scope of the invention in any manner.

EXAMPLES

Expression Vector Containing Human IFN-β ($phe_{101}$)

We used plasmid pBG311 as the expression vector. A full description of pBG311 is given in Cate et al., "Isolation Of The Bovine And Human Genes For Mullerian Inhibiting Substance And Expression Of The Human Gene In Animal Cells", *Cell*, 45, pp. 685–98 (1986). The vector uses the SV40 early promoter, splice signal, and polyadenylation signal and was constructed using pAT153 as backbone.

A DNA fragment containing the DNA sequence shown in FIG. 2 (SEQ ID NO: 2) was cloned into pBG311 and operatively linked to the SV40 early promoter through a DNA sequence encoding the signal sequence for native IFN-β according to standard protocols. The resulting expression vector was designated pBeta-phe. The IFN-β mutein DNA sequence (SEQ ID NO: 2) encodes an IFN-β mutein having an amino acid sequence identical to wild type IFN-β except that the val (V) at position 101, numbered in accordance with wild type IFN-β, is substituted with phe (F). The mutein encoded by this sequence is designated IFN-β (phe$_{101}$).

Competent *Escherichia coli* (SURE™, Stratagene) were transformed with the pBeta-phe plasmid according to standard procedures. Colonies containing the pBeta-phe plasmid (i.e., containing a DNA sequence encoding IFN-β(phe$_{10}$l) were identified by hybridization to a oligonucleotide probe specific for IFN-β(phe$_{101}$) using a standard protocol (Grunstein and Hogness, 1975).

Amplification Vector

We used plasmid pAdD26SV(A)-3 to amplify the IFN-β (phe$_{101}$) gene in our ultimate transformants. This plasmid is described in Kaufman and Sharp, "Construction Of A Modular Dihydrafolate Reductase cDNA Gene: Analysis Of Signals Utilized For Efficient Expression", *Mol. Cell. Biol.*, 2, pp. 1304–19 (1982) and in U.S. Pat. No. 4,740,461. The plasmid expresses murine dihydrofolate reductase (DHFR) under the transcriptional control of the Adenovirus 2 (Ad2) major late promoter (MLP). A 5' splice site, derived from an immunoglobulin variable region gene, is located between the Ad2 MLP and the DHFR coding sequences. The SV40 polyadenylation site is present downstream of the DHFR gene. The plasmid contains the prokaryotic origin of replication (ori) and tetracycline resistance gene from pBR322.

Transformation Of A Cell Line

The CHO-DUKX-B1 DHFR⁻ cell line was cotransformed with the pBeta-phe plasmid and plasmid pAdD26SV(a)-3. This cell line was derived from the wild type CHO-K1 cell line by ethyl methanesulfonate and UV irradiation induced mutagenesis. See Chasin and Urlaub, "Isolation Of Chinese Hamster Cell Mutants Deficient In Dihydrofolate Reductase Activity", *Proc. Natl. Acad. Sci. USA*, 77, pp. 4216–20 (1980). Dihydrofolate reductase catalyzes the conversion of folate to tetrahydrofolate. Cells without functional DHFR require exogenous ribonucleosides and deoxyribonucleosides for growth. Inhibition of growth can be induced by methotrexate, a folate analogue, which binds to and inhibits DHFR. Titration of methotrexate can lead to methotrexate resistance by amplification of the DHFR gene. (Kaufman & Sharp, 1982, supra). Amplification and increased expression of genes near DHFR often occurs when DHFR is amplified. Therefore, cells resistant to high levels of methotrexate often demonstrate increased specific productivity of nearby genes.

The pBeta-phe plasmid (restricted with Xmnl) and plasmid pAdD26SV(a)-3 (restricted with Stul) were mixed in a ratio of 10:1, respectively. The DNA was transformed into CHO-DUKX-B1 DHFR⁻ cells by electroporation. Cells were plated in non-selective α+ medium (α MEM base plus ribonucleosides and deoxyribonucleosides, 10% fetal bovine serum [FBS], 4 mM glutamine) and allowed to grow for 2 days. The medium was then exchanged for α⁻ medium (α MEM base without ribonucleosides and deoxyribonucleosides, 10% FBS, 4 mM glutamine)+50 nM methotrexate (MTX). The cells were removed by trypsinization and plated at ca. 8×10⁵ cells/10 cm tissue culture plate. After 14 days, clones were picked and grown in 96 well tissue culture plates. One clone was expanded into a 12 well tissue culture plate and then 7 days later put into a 6 well tissue culture plate in the presence of 250 nM MTX. This clone was expanded into a T75 flask (grown in α⁻ medium+ 250 nM MTX) and then amplified in 750 nM MTX. A subclone was picked into a 96 well tissue culture plate, expanded into a 48 well tissue culture plate, then a 6 well tissue culture plate and then a T75 tissue culture flask.

Purification Of IFN-β(phe$_{101}$)

IFN-β(phe$_{101}$), produced by culturing the above subclone (or others similar to it) and then secreted into the culture medium, can be purified by immunoaffinity chromatography, substantially as described by Okamura et al., "Human Fibroblastoid Interferon: Immunosorbent Column Chromatography And N-Terminal Amino Acid Sequence", *Biochem.*, 19, pp. 3831–35 (1980).

CNBr-Sepharose 4B resin (2 g, 7 ml) is prepared by suspending in 1 mM HCl. The gel is washed with 1 mM HCl for 15 min on a scintered glass filter. Anti-IFN-β mabs (such as B02, Yamasa, Japan) are coupled to CNBr-Sepharose 4B resin by incubating in coupling buffer (100 mM NaHCO₃, pH 8.3, 500 mM NaCl) for 2 hours at room temperature on a rocker platform. Typically, 1–2 mg IFN-β mab per ml of resin is coupled, but this amount can be varied. The unreacted CNBr is blocked with 100 mM Tris-HCl, pH 8, 500 mM NaCl, overnight at 4° C. Alternately, the unreacted CNBr is blocked with 100 mM ethanolamine under substantially the same conditions.

The coupled resin is washed with three cycles of alternative pH. Each cycle consists of a wash with acetate buffer (100 mM, pH 4) containing 500 mM NaCl followed by a wash with Tris buffer (100 mM, pH 8) containing 500 mM NaCl.

A 1 cm×3 cm column (2.3 ml bed volume) is prepared with the coupled resin. The column is equilibrated with PBS (greater than 5 column volumes). IFN-β(phe$_{101}$)-containing samples are diluted 1:3 in equilibration buffer, pH 6.8 and loaded. The load is chased with PBS, washed with 20 mM K₂HPO₄, 1 M NaCl, pH 6.8, and eluted with 200 mM Na citrate, pH 2. The pH of the eluate was adjusted to 6 by diluting the sample with 500 mM Mes, pH 6.

Characterization By Peptide Mapping

An IFN-β(phe$_{101}$), mutein that had been produced and purified in a different and less preferred manner than described above was characterized by peptide mapping. A 30 μg aliquot of IFN-β(phe$_{101}$) or wild type IFNβ sample was lyophilized, suspended in 200 μl of endoproteinase Lys-C digestion buffer (100 mM TRIS, pH 9, 0.5 mM EDTA), incubated for 12 hours at 22° with 1.5 μg of endoproteinase Lys-C and subjected to mapping analysis on a C₈ reversed phase HPLC column (0.45×25 cm). The column was developed with a 30 minute, 0–70% gradient of acetonitrile in 0.1% TFA at 1.4 mls/min. The column effluent was monitored at 214 nm. FIG. 4, Panel A shows a portion of the peptide map for IFN-β(phe$_{101}$) with the arrowhead indicating the peptide TFLEEK (SEQ ID NO: 3). This peak did not occur in the peptide map for wild type IFN-β. FIG. 4, Panel B shows the corresponding region of a peptide map for wild type IFN-β with the arrowhead indicating the peptide TVLEEK (SEQ ID NO: 4). The identity of the TFLEEK and TVLEEK were verified by protein sequence analysis. We estimate that the β-Phe$_{101}$ and wild type β-IFN were greater than 98% pure. Protein concentrations were estimated from absorbance at 280 nm using an extinction coefficient of 1.5 for a 1 mg solution. In order to stabilize the proteins for biological studies, they were diluted to 4 μg/ml in PBS containing 5% FBS and 5 mM HEPES, pH 7.5.

Antiviral Activity Of IFN-β(phe$_{101}$) In The CPE Assay

The preparation of IFN-β(phe$_{101}$) that was characterized by peptide mapping was analyzed in a Cytopathic Effect (CPE) assay for antiviral activity. A wild type recombinant IFN-β standard was prepared in Dulbecco's Modified Eagle Medium (DMEM), 10% FBS, 4 mM glutamine at a concentration of 10,000 units/mL and stored in aliquots at −70° C. On day 1, standard, control and IFN-β$_{Phe}$ samples were diluted in DMEM, 10% FBS, 4 mM glutamine in three dilution series: i) starting at 64 units/mL followed by 2-fold dilutions, ii) starting at 12 units/mL followed by 1.5-fold dilutions, and iii) starting at 6 units/mL followed by 1.2-fold dilutions. Fifty microliters of the dilutions were then added in columns to the wells of 96-well microtiter plates. A549 cells were added to each well at $10^5$ cells/ml, 50 uL per well, in DMEM, 10% FBS, 4 mM glutamine and the cells are incubated at 37° C., 5% $CO_2$ for 15 to 20 hours.

The plate contents were shaken into a bleach bucket and 100 uL encephalomyocarditis virus (EMC virus) at appropriate dilution in media was added to each well. The virus and cells were incubated at 37° C., 5% $CO_2$ for 30 hours. The plate contents were then shaken into a bleach bucket and 0.75% crystal violet dye added to the plates. After 5 to 10 minutes, the plates were washed with distilled water and allowed to dry before being read visually.

Samples and standards were tested in duplicate on each assay plate, yielding two data points per dilution series per assay day.

Figure 5:
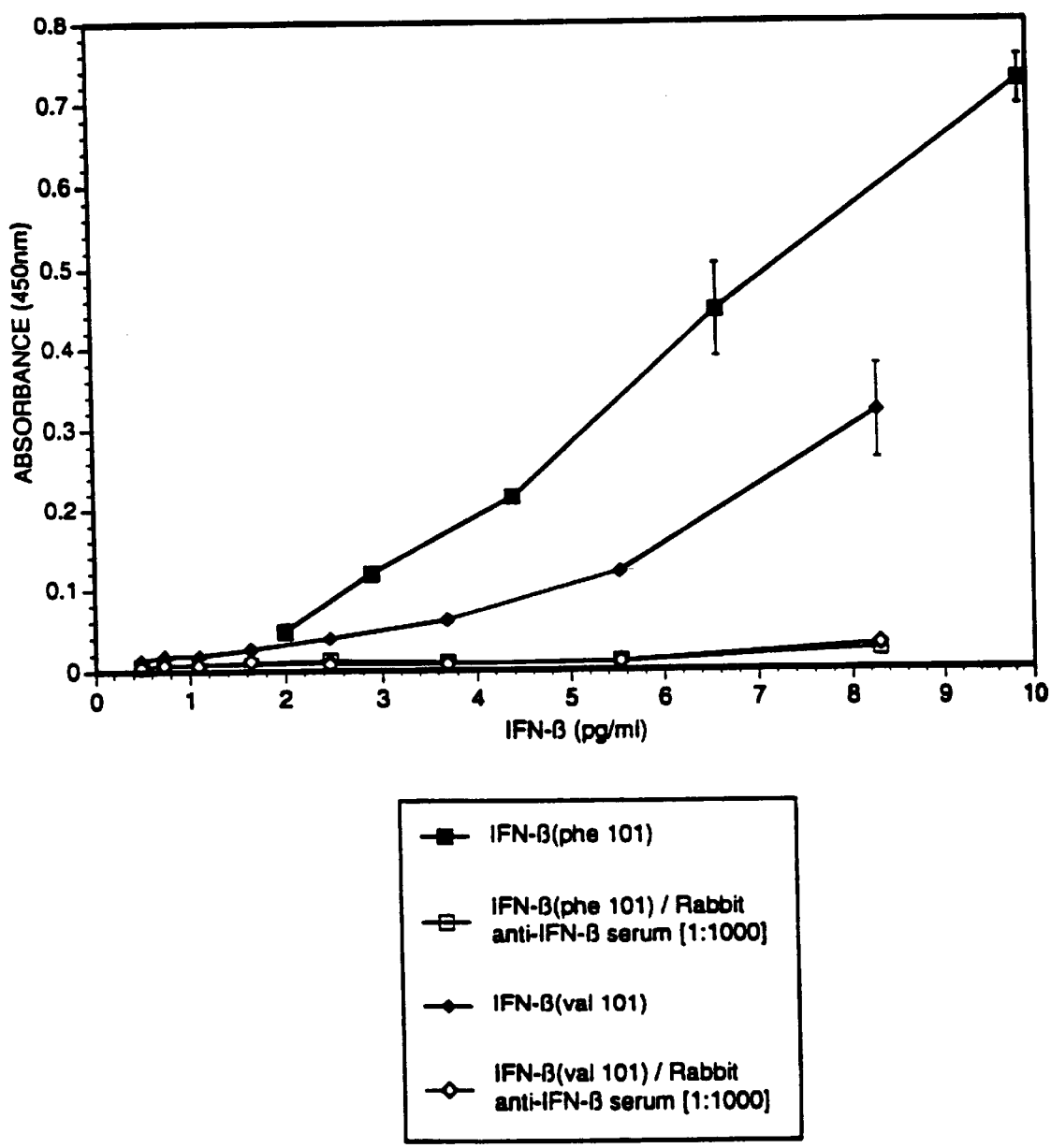
FIG. 5 shows that antibodies to wild type IFN-β neutralize the activity of IFN-β(phe$_{101}$) and wild type IFN-β.

IFN-β(phe$_{101}$) was tested in 14 assays in duplicate. Wild type recombinant IFN-β was used as a standard. Based on these experiments, IFN-β(phe$_{101}$) had a specific activity of $4.8 \times 10^8$ U/mg with a 95% confidence interval of $3.5$–$6.7 \times 10^8$. Wild type IFN-β had a specific activity of approximately $2.0 \times 10^8$ units/mg with a confidence interval of $1.6$–$2.5 \times 10^8$. The data in FIG. 5 show a similar result. The media used was Dulbecco's Modified Eagle Medium (DMEM), 10% FBS, 4 mM glutamine. The cell containing plates were then incubated at 37° C., 5% $CO_2$ for approximately 24 hours.

B. Preparation Of Master Plates

Master plates containing either sample or standard were then created with serially diluted wells (in duplicate). Sample wells contained either purified recombinant mutein IFN-β(phe$_{101}$) or wild type recombinant IFN-β(val$_{101}$) in the presence or absence of rabbit anti-IFN-β polyclonal sera. Control wells contained either buffer alone or recombinant wild type IFN-β (as a standard) in the presence or absence of an anti-LFA3 antibody (data not shown).

Serial dilutions were performed as follows. 200 microliters of control, or of wild type or mutein IFN-β sample (at a concentration of about 25 pg/ml), was added to each well in row A on each plate. The final concentration of sample in row A was 8.5 pg/ml. Dilutions of 1:1.5 were then performed down each plate.

C. Antibodies To Wild Type IFN-β

Antibodies to wild type IFN-β(val$_{101}$) were produced in rabbits immunized with recombinant wild type IFN-β (val$_{101}$). Rabbit anti-IFN-β polyclonal sera was collected from the immunized rabbits at appropriate intervals, pooled and stored until use (Rabbit IFN-β serum pool 6/25/93; 5 ml/vial, 0.02% azide; ref. 0.01742.062).

D. Sample/Ab Incubation

Rabbit anti-IFN-β polyclonal sera was added to the appropriate wells on the Master plates. The final dilution of antibody was 1:1000. The The specific activity of recombinant IFN-β(phe$_{101}$) is on average about 2.5 fold higher than that of recombinant wild type IFN-β, as measured in our antiviral assay.

Analysis Of IFN-β(phe$_{101}$) For Receptor Binding

The IFN-β(phe$_{101}$) used in the CPE assay above was also analyzed for ability to bind to cells that express interferon receptors. For these studies we examined the binding of either wild type $^{125}$I-IFN-β or $^{125}$I-IFN-β(phe$_{101}$) to Daudi cells or A549 cells (FIG. 3). Carrier-free IFN-β was iodinated substantially according to the chloramine T method. Unreacted iodine was removed by size exclusion chromatography on a Superdex 75 column that was equilibrated in PBS containing 1 mg/ml bovine serum albumin. The concentration of the iodinated IFN-β was determined by the CPE assay, assuming a specific activity of $2 \times 10^8$ units/mg. Normally 5 ng (1 μL, 300,000 cpm) of iodinated IFN-β (either alone or in the presence of a 50 fold excess of non-iodinated interferon) was added to 1.7 mL eppendorf tubes in a total volume of less than 10 μL. The labelled ligand was allowed to bind alone (−) or was competed with unlabeled IFN-β(phe$_{101}$), α2-IFN (α2), γ-IFN (γ) or wild type recombinant IFN-β (WT).

Both Daudi cells and A549 cells (American Type Culture Collection) were used. The cells were suspended in DMEM/ 5% FBS at $2 \times 10^6$ cells/mL. To the samples of the IFN-β, 0.5 mL of the cell suspension was added. The tubes were mixed by inversion and incubated at ambient temperature for 45 minutes. The cells were then pelleted at 1000×g for 2 min and washed two times with 0.5 mL DMEM/10% FBS. Each wash was followed by a centrifugation step at 1000×g for 2 min. The cells were resuspended in 0.1 mL, transferred into tubes for counting and binding quantified in a Beckman gamma 407 counter.

The data suggest that the binding of IFN-β(phe$_{101}$) is very similar to that of wild type IFN-β on both cell types. Comparable amounts of wild type $^{125}$I-IFN-β and $^{125}$I-IFN-β(phe$_{101}$) were bound and competed similarly by noniodinated α-IFN, wild type IFN-β and IFN-β(phe$_{101}$). The binding was not affected by the addition of recombinant human γ-IFN.

The Antiviral Activity of IFN-β(phe$_{101}$) Is Substantially Neutralized by Antibodies to Wild Type IFN-β

A number of preparations of recombinant mutein IFN-β (phe$_{101}$) produced in CHO cells as described above were purified to approximately 90% purity using column chromatography. These samples were diluted to 25 pg/ml. Wild type recombinant IFN-β, designated here as IFN-β(val$_{101}$), was produced and purified in substantially the same way.

Standard antiviral and antibody neutralization assays were used to demonstrate that antibodies to wild type IFN-β(val$_{101}$) at least partially neutralize IFN-β(phe$_{101}$). The particular antiviral assay and neutralization assay that we used, detailed below, are substantially the same as the antiviral and antibody neutralization assays described in European patent EP B1 41313. See p. 26, lines 1–21; p. 29, line 48—p. 32, line 3.

A. Preparation Of Cell-containing Plates

A549 cells (ATCC CCL185) were seeded into 96 well plates at 3×10$^4$ cells/100 microliter media/well. antibody/IFN-β mixture was incubated at room temperature for 45 minutes.

E. Incubation Of Cells With Control, Sample Or Sample/Ab

The media was then aspirated from the cell-containing plates prepared and replaced with aliquots (100 μl/well) of control, IFN-β sample or IFN-β/Ab sample, as appropriate, from the Master plates prepared. The cell-containing plates were incubated at 37° C., 5% $CO_2$ for 16–24 hours.

F. Viral Challenae

The next step was the viral challenge. The cell-containing plate contents were then aspirated and 100 μl of a solution of encephalomyocarditis virus (EMCV) at appropriate dilution was added to each well. The virus and cells were incubated at 37° C., 5% $CO_2$ for 41–45 hours.

The cell-containing plates were developed using the XTT/PMS colorimetric method. A 1 mg/ml XTT (3,3-[1-(phenylamino)carbonyl]-3,4-tetrazolium]-bis-(4-methoxy-6-nitro)-benzenesulfonic acid; Sigma) solution was prepared in phosphate buffered saline solution. A 1 mg/ml PMS (phenazine methosulfate) solution was prepared in water. A PMS/XTT solution was prepared at 1:50. The development solution was prepared by diluting the PMS/XTT 1:3 in phosphate buffered saline solution. The tetrazolium compound XTT is reduced by living cells to form an orange colored formazon. Color formation correlates directly to viable cell number.

The cell-containing plates were aspirated and washed with 150 μl/well of phosphate buffered saline solution. Each well then received 150 μl of development solution. The plates were incubated at 37° C., 5% $CO_2$ for 30–60 minutes.

Absorbance at 450 nm was measured on a Molecular Devices Thermo$_{max}$ microplate reader with Softmax software. The results are displayed graphically in FIG. 5. Absorbance is plotted against IFN-β concentration.

FIG. 5 shows that in the absence of rabbit anti-IFN-β polyclonal sera, samples of mutein IFN-β(phe$_{101}$) (closed square; ■) and of wild type IFN-β(val$_{101}$) (closed diamond; ♦) protected the A549 cells from the EMCV. This is indicated by the increase in absorbance (indicating more living cells) with increasing mutein IFN-β or wild type IFN-β concentration.

FIG. 5 also shows that in the presence of rabbit anti-IFN-β polyclonal sera, samples of mutein IFN-β(phe$_{101}$) (open square; □) and of wild type IFN-β(val$_{101}$) (open diamond; ◇) failed to protect the A549 cells from the EMCV. This is shown by the baseline absorbance value for any mutein IFN-β or wild type IFN-β concentration, indicating that almost all A549 cells were dead.

In sum, FIG. 5 shows that the antiviral activity of mutein IFN-β(phe$_{101}$) was neutralized by antibodies to wild-type IFN-β (i.e., rabbit anti-IFN-β antibodies).

Treatment Of Restenosis With IFN-β Mutein Gene Therapy

Initial testing of gene therapy for restenosis is conducted in a pig model using recombinant wild type porcine IFN-β according to the following protocol.

Cell proliferation is measured by immunohistochemistry. All animals receive an intravenous infusion of BrdC (Sigma, St. Louis, Mo.), 25 mg/kg total dose, 1 hour before death. Immunohistochemistry with monoclonal antibody to BrdC (1:1000 dilution, Amersham Life Sciences, Arlington Heights, Ill.) is performed to label nuclei in proliferating cells as described in Goncharoff et al., *J. Immunol. Methods*, 93, p. 97 (1988). Identification of vascular smooth muscle cells is performed by immunohistochemistry with an antibody to smooth muscle α-actin (1:500 dilution, Boehringer Mannheim, Germany) as described in Islk et al., *Am. J. Pathol.*, 141, p. 1139 (1992).

Domestic Yorkshire pigs (12 to 15 kg) are anesthetized with zolazepamin-tiletamine (6.0 mg/kg) in combination with (2.2 mg/kg intramuscular) rompun with 1% nitrous oxide. The iliofemoral arteries are exposed by sterile surgical procedures, and a double-balloon catheter is inserted into the iliofemoral artery as described in Nabel et al., *Science*, 249, p. 1285 (1990). The proximal balloon is inflated to 300 mm Hg, as measured by an on-line pressure transducer, for 5 min. The balloon is deflated and the catheter is advanced so that the central space between the proximal and distal balloon now occupies the region of previous balloon injury. Both balloons are inflated, and the segment is irrigated with heparinized saline. The adenoviral inoculum is instilled for 20 min in the central space of the catheter. The catheter is removed and antegrade blood flow as restored.

The injured arteries of all pigs are infected with $10^{10}$ plaque-forming units (PFU) per milliliter of an ADV-ΔE1 vector containing an insert encoding porcine IFN-β or with an ADV-ΔE1 vector lacking the insert. In each animal, both iliofemoral arteries are transfected with the same vector at a titer of $1×10^{10}$ PFU/ml and 0.7 ml is used in each animal (final dose of $7×10^9$ PFU).

The vessel segments in these pigs are excised 21 or 42 days later. Each artery is processed in an identical manner. The region of instillation between the two double balloons is cut into five cross-sections of identical size. Sections 1 and 4 are fixed in methyl Carnoy and sections 3 and 5 are fixed in formalin, and all sections are paraffin-embedded and stained with hematoxylin-eosin. Additional antibody studies are performed on methyl Carnoy- or formalin-fixed arteries. Tissue from section 2 is flash-frozen in liquid nitrogen and stored at −80° C. for DNA isolation. Measurements of intimal and medial area are determined in four sections from each artery in a blinded manner by two independent readers, and the measurements for each artery are averaged. Slides of arterial specimens are studied with a microscope-based video imaging analysis system (Image-1 System, Universal Imaging, Weschester, Pa.) as described in Nabel et al., *Proc. Natl. Acad. Sci U.S.A.*, 90, p. 10759 (1993).

As an alternative to the above-described adenoviral-based Ad-ΔE1 vector, direct gene transfer may also be used. One suitable construct is a plasmid derived from the RSV backbone, with the RSV-LTR promoter driving expression of IFN-β, with the SV-40 poly A' signal 3' to the IFN-β DNA sequence. See, e.g., Gorman et al., *Science*, 221, pp. 551–53 (1983).

The above protocol is then modified so that the vector contains a DNA insert encoding the human IFN-β muteins of this invention for gene therapy in humans.

Sequences

The following is a summary of the sequences set forth in the Sequence Listing:

SEQ ID NO:1—Amino acid sequence of IFN-β(phe$_{101}$)

SEQ ID NO:2—DNA sequence encoding IFN-β(phe$_{101}$), including DNA sequence encoding the signal sequence of native IFN-β

SEQ ID NO:3—Amino acid sequence of IFN-β(phe$_{101}$)

SEQ ID NO:4—Amino acid sequence of peptide TFLEEK.

SEQ ID NO:5—Amino acid sequence of peptide TVLEEK.

Deposits

*E. coli* K-12 containing plasmid pBeta-phe (which contains a DNA sequence encoding IFN-β(phe$_{101}$) and the native IFN-β signal sequence) has been deposited. The deposit was made in accordance with the Budapest Treaty and was deposited at the American Type Culture Collection, Rockville, Md., U.S.A. on Mar. 11, 1994. The deposit received the accession number 69584.

The foregoing description has been presented only for purposes of illustration and description. This description is not intended to limit the invention to the precise form disclosed. It is intended that the scope of the invention be defined by the claims appended hereto.

What is claimed is:

1. A method for induction of an antiviral immune response in a patient comprising administration of an immunomodulation effective amount of an IFN-β mutein, wherein the IFN-β mutein has a phe (F), tyr (Y), trp (W), or his (H) substituted for the val (V) at position 101 in wild type IFN-β, numbered in accordance with wild type IFN-β, and wherein the administration results in an anitiviral immune response.

2. A method for induction of an immune response in a patient comprising administration of an immunomodulation effective amount of an IFN-β mutein, wherein the IFN-β mutein has a phe (F), tyr (Y), trp (W), or his (H) substituted for the val (V) at position 101 in wild type IFN-β, numbered in accordance with wild type IFN-β, and wherein the administration results in induction of an immune response.

3. The method according to claim 1 or 2, wherein the val (V) is substituted with phe (F).

4. The method according to claim 1 or 2, wherein the mutein comprises the amino acid sequence: Met-Ser-Tyr-Asn-Leu-Leu-Gly-Phe-Leu-Gln-Arg-Ser-Ser-Asn-Phe-Gln-Cys-Gln-Lys-Leu-Leu-Trp-Gln-Leu-Asn-Gly-Arg-Leu-Glu-Tyr- Cys-Leu-Lys-Asp-Arg-Met-Asn-Phe-Asp-Ile-Pro-Glu-Glu-Ile-Lys- Gln-Leu-Gln-Gln-Phe-Gln-Lys-Glu-Asp-Ala-Ala-Leu-Thr-Ile-Tyr- Glu-Met-Leu-Gln-Asn-Ile-Phe-Ala-Ile-Phe-Arg-Gln-Asp-Ser-Ser- Ser-Thr-Gly-Trp-Asn-Glu-Thr-Ile-Val-Glu-Asn-Leu-Leu-Ala-Asn- Val-Tyr-His-Gln-Ile-Asn-His-Leu-Lys-Thr-Phe-Leu-Glu-Glu-Lys- Leu-Glu-Lys-Glu-Asp-Phe-Thr-Arg-Gly-Lys-Leu-Met-Ser-Ser-Leu- His-Leu-Lys-Arg-Tyr-Tyr-Gly-Arg-Ile-Leu-His-Tyr-Leu-Lys-Ala- Lys-Glu-Tyr-Ser-His-Cys-Ala-Trp-Thr-Ile-Val-Arg-Val-Glu-Ile- Leu-Arg-Asn-Phe-Tyr-Phe-Ile-Asn-Arg-Leu-Thr-Gly-Tyr-Leu-Arg-Asn (SEQ ID NO:1).

5. A method for treating a disease selected from the aroup consisting of osteosarcoma, cervical dysplasia, leukemia, multiple myeloma, basal cell carcinoma, lymphoid malignancies, breast carcinoma, glioma, melanoma, papilloma virus, hepatitis, viral encephalitis, cytomegalovirus, herpes infections, and multiple sclerosis, in a patient comprising administration of an effective amount of an IFN-β mutein, wherein the IFN-β mutein has phe (F), tyr (Y), trp (W) or his (H) substituted for the val (V) at position 101 in wild type IFN-β, numbered in accordance with wild type IFN-β, and wherein the administration results in a theranoutic benefit.

6. A method for inhibiting the neoplastic growth of cells in a patient comprising administration of an effective amount of an IFN-β mutein, wherein the IFN-β mutein has phe (F), tyr (Y), trp (W) or his (H) substituted for the val (V) at position 101 in wild type IFN-β, numbered in accordance with wild type IFN-β, and wherein the administration results in a therapeutic benefit.

7. The method according to claims 5 or 6, wherein the val (V) is substituted with phe (F).

8. The method according to claims 5 or 6, wherein the mutein comprises the amino acid sequence: Met-Ser-Tyr-Asn-Leu-Leu-Gly-Phe-Leu-Gln-Arg-Ser-Ser-Asn-Phe-Gln-Cys-Gln-Lys-Leu-Leu-Trp-Gln-Leu-Asn-Gly-Arg-Leu-Glu-Tyr- Cys-Leu-Lys-Asp-Arg-Met-Asn-Phe-Asp-Ile-Pro-Glu-Glu-Ile-Lys- Gln-Leu-Gln-Gln-Phe-Gln-Lys-Glu-Asp-Ala-Ala-Leu-Thr-Ile-Tyr- Glu-Met-Leu-Gln-Asn-Ile-Phe-Ala-Ile-Phe-Arg-Gln-Asp-Ser-Ser- Ser-Thr-Gly-Trp-Asn-Glu-Thr-Ile-Val-Glu-Asn-Leu-Leu-Ala-Asn- Val-Tyr-His-Gln-Ile-Asn-His-Leu-Lys-Thr-Phe-Leu-Glu-Glu-Lys- Leu-Glu-Lys-Glu-Asp-Phe-Thr-Arg-Gly-Lys-Leu-Met-Ser-Ser-Leu- His-Leu-Lys-Arg-Tyr-Tyr-Gly-Arg-Ile-Leu-His-Tyr-Leu-Lys-Ala- Lys-Glu-Tyr-Ser-His-Cys-Ala-Trp-Thr-Ile-Val-Arg-Val-Glu-Ile- Leu-Arg-Asn-Phe-Tyr-Phe-Ile-Asn-Arg-Leu-Thr-Gly-Tyr-Leu-Arg-Asn (SEQ ID NO:1).

* * * * *

UNITED STATES PATENT AND TRADEMARK OFFICE
CERTIFICATE OF CORRECTION

PATENT NO.      : 6,127,332
DATED           : October 3, 2000
INVENTOR(S)     : Goelz, et al.

Page 1 of 1

It is certified that error appears in the above-identified patent and that said Letters Patent is hereby corrected as shown below:

<u>Title page, item [56],</u>
After item [56] References Cited, and before item [57] Abstract, please recognize Scott D. Miller as an associate attorney.

Signed and Sealed this

Twenty-fifth Day of September, 2001

*Attest:*

*Nicholas P. Godici*

*Attesting Officer*

NICHOLAS P. GODICI
*Acting Director of the United States Patent and Trademark Office*

UNITED STATES PATENT AND TRADEMARK OFFICE
CERTIFICATE OF CORRECTION

PATENT NO. : 6,127,332 Page 1 of 1
DATED : October 3, 2000
INVENTOR(S) : Susan E. Goelz et al.

It is certified that error appears in the above-identified patent and that said Letters Patent is hereby corrected as shown below:

Title page,
Item [56] change "James F. Hanley," to -- James F. Haley, --;

Column 21,
Line 26, change "claim" to -- claims --;
Line 28, change "claim" to -- claims --;

Column 22,
Line 18, change "theranou-tic" to -- therapeu-tic --.

Signed and Sealed this

Twenty-first Day of May, 2002

*Attest:*

*Attesting Officer*

JAMES E. ROGAN
*Director of the United States Patent and Trademark Office*

```
                         SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
        (A) LENGTH: 166 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:1:

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Phe Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

(2) INFORMATION FOR SEQ ID NO:2:
```

(i) SEQUENCE CHARACTERISTICS:
        (A) LENGTH: 561 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: sig_peptide
        (B) LOCATION: 1..63

(ix) FEATURE:
        (A) NAME/KEY: mat_peptide
        (B) LOCATION: 64..561

(ix) FEATURE:
        (A) NAME/KEY: CDS
        (B) LOCATION: 1..561

(xi) SEQUENCE DESCRIPTION: SEQ ID NO:2:

```
ATG ACC AAC AAG TGT CTC CTC CAA ATT GCT CTC CTG TTG TGC TTC TCC        48
Met Thr Asn Lys Cys Leu Leu Gln Ile Ala Leu Leu Leu Cys Phe Ser
-21 -20              -15                  -10

ACT ACA GCT CTT TCC ATG AGC TAC AAC TTG CTT GGA TTC CTA CAA AGA        96
Thr Thr Ala Leu Ser Met Ser Tyr Asn Leu Leu Gly Phe Leu Gln Arg
 -5              1               5                   10

AGC AGC AAT TTT CAG TGT CAG AAG CTC CTG TGG CAA TTG AAT GGG AGG       144
Ser Ser Asn Phe Gln Cys Gln Lys Leu Leu Trp Gln Leu Asn Gly Arg
             15                  20                  25

CTT GAA TAC TGC CTC AAG GAC AGG ATG AAC TTT GAC ATC CCT GAG GAG       192
Leu Glu Tyr Cys Leu Lys Asp Arg Met Asn Phe Asp Ile Pro Glu Glu
         30                  35                  40

ATT AAG CAG CTG CAG CAG TTC CAG AAG GAG GAC GCC GCA TTG ACC ATC       240
Ile Lys Gln Leu Gln Gln Phe Gln Lys Glu Asp Ala Ala Leu Thr Ile
             45                  50                  55

TAT GAG ATG CTC CAG AAC ATC TTT GCT ATT TTC AGA CAA GAT TCA TCT       288
Tyr Glu Met Leu Gln Asn Ile Phe Ala Ile Phe Arg Gln Asp Ser Ser
 60                  65                  70                  75

AGC ACT GGC TGG AAT GAG ACT ATT GTT GAG AAC CTC CTG GCT AAT GTC       336
Ser Thr Gly Trp Asn Glu Thr Ile Val Glu Asn Leu Leu Ala Asn Val
                 80                  85                  90

TAT CAT CAG ATA AAC CAT CTG AAG ACA TTC CTG GAA GAA AAA CTG GAG       384
Tyr His Gln Ile Asn His Leu Lys Thr Phe Leu Glu Glu Lys Leu Glu
             95                 100                 105

AAA GAA GAT TTC ACC AGG GGA AAA CTC ATG AGC AGT CTG CAC CTG AAA       432
Lys Glu Asp Phe Thr Arg Gly Lys Leu Met Ser Ser Leu His Leu Lys
        110                 115                 120

AGA TAT TAT GGG AGG ATT CTG CAT TAC CTG AAG GCC AAG GAG TAC AGT       480
Arg Tyr Tyr Gly Arg Ile Leu His Tyr Leu Lys Ala Lys Glu Tyr Ser
        125                 130                 135

CAC TGT GCC TGG ACC ATA GTC AGA GTG GAA ATC CTA AGG AAC TTT TAC       528
His Cys Ala Trp Thr Ile Val Arg Val Glu Ile Leu Arg Asn Phe Tyr
140                 145                 150                 155

TTC ATT AAC AGA CTT ACA GGT TAC CTC CGA AAC                           561
Phe Ile Asn Arg Leu Thr Gly Tyr Leu Arg Asn
                160                 165
```

(2) INFORMATION FOR SEQ ID NO:3:

(i) SEQUENCE CHARACTERISTICS:
        (A) LENGTH: 187 amino acids (B) TYPE: amino acid
            (D) TOPOLOGY: linear (ii) MOLECULE TYPE: protein (xi) SEQUENCE DESCRIPTION: SEQ ID NO:3:

Met Thr Asn Lys Cys Leu Leu Gln Ile Ala Leu Leu Leu Cys Phe Ser
-21 -20              -15                  -10

Thr Thr Ala Leu Ser Met Ser Tyr Asn Leu Leu Gly Phe Leu Gln Arg
 -5                   1               5                   10

Ser Ser Asn Phe Gln Cys Gln Lys Leu Leu Trp Gln Leu Asn Gly Arg
             15                  20                  25

Leu Glu Tyr Cys Leu Lys Asp Arg Met Asn Phe Asp Ile Pro Glu Glu
         30                  35                  40

Ile Lys Gln Leu Gln Gln Phe Gln Lys Glu Asp Ala Ala Leu Thr Ile
     45                  50                  55

Tyr Glu Met Leu Gln Asn Ile Phe Ala Ile Phe Arg Gln Asp Ser Ser
 60                  65                  70                  75

Ser Thr Gly Trp Asn Glu Thr Ile Val Glu Asn Leu Leu Ala Asn Val
             80                  85                  90

Tyr His Gln Ile Asn His Leu Lys Thr Phe Leu Glu Glu Lys Leu Glu
             95                 100                 105

Lys Glu Asp Phe Thr Arg Gly Lys Leu Met Ser Ser Leu His Leu Lys
            110                 115                 120

Arg Tyr Tyr Gly Arg Ile Leu His Tyr Leu Lys Ala Lys Glu Tyr Ser
    125                 130                 135

His Cys Ala Trp Thr Ile Val Arg Val Glu Ile Leu Arg Asn Phe Tyr
140                 145                 150                 155

Phe Ile Asn Arg Leu Thr Gly Tyr Leu Arg Asn
            160                 165

(2) INFORMATION FOR SEQ ID NO:4:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:4:

Thr Phe Leu Glu Glu Lys
1               5

(2) INFORMATION FOR SEQ ID NO:5:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (iii) HYPOTHETICAL: NO -continued

```
    (iv) ANTI-SENSE: NO (xi) SEQUENCE DESCRIPTION: SEQ ID NO:5:

Thr Val Leu Glu Glu Lys
1               5
```